United States Patent
Kim et al.

(10) Patent No.: US 10,072,278 B2
(45) Date of Patent: Sep. 11, 2018

(54) STRAIN HAVING ENHANCED L-VALINE PRODUCTIVITY AND L-VALINE PRODUCTION METHOD USING THE SAME

(71) Applicant: CJ Cheiljedang Corporation, Seoul (KR)

(72) Inventors: Hye Won Kim, Gyeonggi-do (KR); Ji Hye Lee, Gyeonggi-do (KR); Byeong Cheol Song, Gyeonggi-do (KR); Jong Hyun Kim, Gyeonggi-do (KR); Han Hyoung Lee, Seoul (KR); Ae Ji Jeon, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 93 days.

(21) Appl. No.: 14/771,969

(22) PCT Filed: Mar. 5, 2014

(86) PCT No.: PCT/KR2014/001793
§ 371 (c)(1),
(2) Date: Sep. 1, 2015

(87) PCT Pub. No.: WO2014/142463
PCT Pub. Date: Sep. 18, 2014

(65) Prior Publication Data
US 2016/0108444 A1    Apr. 21, 2016

(30) Foreign Application Priority Data

Mar. 11, 2013 (KR) .................. 10-2013-0025528

(51) Int. Cl.
| | |
|---|---|
| *C12P 13/08* | (2006.01) |
| *C07K 7/06* | (2006.01) |
| *C12N 15/52* | (2006.01) |
| *C12N 15/77* | (2006.01) |

(52) U.S. Cl.
CPC ............... *C12P 13/08* (2013.01); *C07K 7/06* (2013.01); *C12N 15/52* (2013.01); *C12N 15/77* (2013.01)

(58) Field of Classification Search
CPC ............................................. C12Y 202/01006
See application file for complete search history.

(56) References Cited

U.S. PATENT DOCUMENTS

2009/0197309 A1    8/2009    Sycheva et al.

FOREIGN PATENT DOCUMENTS

| EP | 0872547 B1 | 12/2007 |
|---|---|---|
| KR | 10-1990-0007948 B | 10/1990 |
| KR | 10-2008-0025355 A | 3/2008 |
| KR | 10-0832740 B1 | 5/2008 |
| KR | 10-1117022 B | 3/2012 |
| WO | WO96-006926 | 3/1996 |
| WO | WO2013-024947 | 2/2013 |

OTHER PUBLICATIONS

Holatko et al. Metabolic engineering of the L-valine biosynthesis pathway in Corynebacterium glutamicum using promoter activity modulation Journal of Biotechnology 139 (2009) 203-210.*
Morbach, et al Attenuation control of ilvBNC in Corynebacterium glutamicum: evidence of leader peptide formation without the presence of a ribosome binding site. J. Biosci. Bioeng. 90, 501-507. 2000 in IDS.*
Park, J. H., et al. Metabolic engineering of *Escherichia coli* for the production of L-valine based on transcriptome analysis and in silico gene knockout simulation. PNAS, vol. 104(19):7797-7802 (May 8, 2007).
Park, J. H. Metabolic engineering of *Escherichia coli* for the production of L-valine based on systems biotechnology. Korea Advanced Institute of Science and Technology, Doctoral Thesis (2007).
Morbach S., et al. Attenuation Control of ilvBNC in *Corynebacterium glutamicum*: Evidence of Leader Peptide Formation without the Presence of a Ribosome Binding Site. Journal of Bioscience and Bioengineering, vol. 90(5):501-507 (2000).
Elisakova, V., et al. Feedback-Resistant Acetohydroxy Acid Synthase Increases Valine Production in *Corynebacterium glutamicum*. Applied and Environmental Microbiology, vol. 71(1), pp. 207-213(2005).
International Search Report dated Jul. 14, 2014 in PCT/KR2014/001793.

* cited by examiner

*Primary Examiner* — Kagnew H Gebreyesus
(74) *Attorney, Agent, or Firm* — Swanson & Bratschun, L.L.C.

(57) ABSTRACT

The present invention relates to a novel L-valine-producing strain which is transformed so as to strengthen the expression of L-valine operon by having a nucleotide sequence, for coding a leader peptide in a regulatory region of ilvBN operon, entirely deleted, or partially deleted or substituted. In addition, the present invention relates to a method for producing L-valine using the novel L-valine-producing strain. According to the novel valine-producing strain and the L-valine production method of the present invention using the strain, there is an advantageous effect of producing L-valine at high efficiency and high yield.

8 Claims, 4 Drawing Sheets

Specification includes a Sequence Listing.

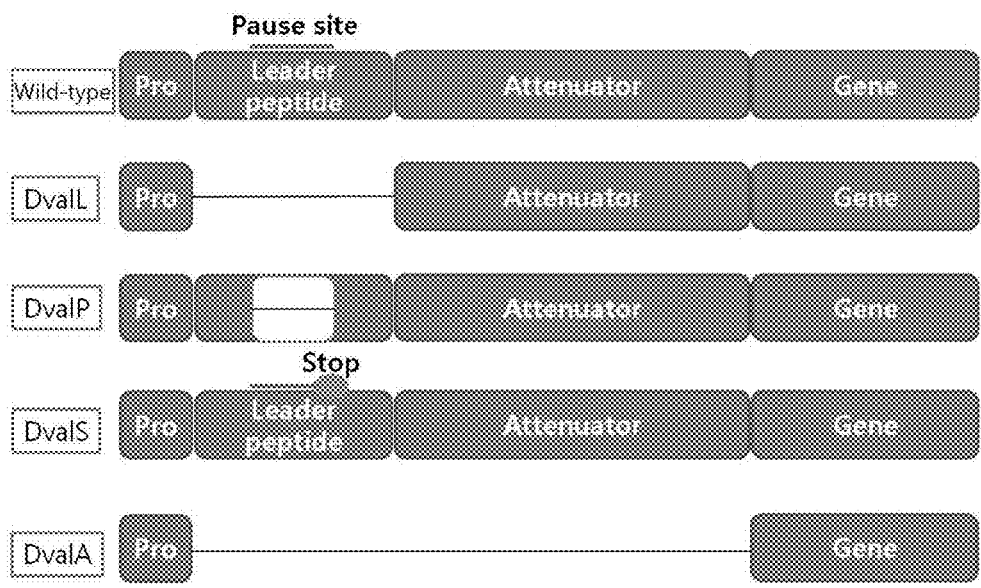

[Fig. 2]
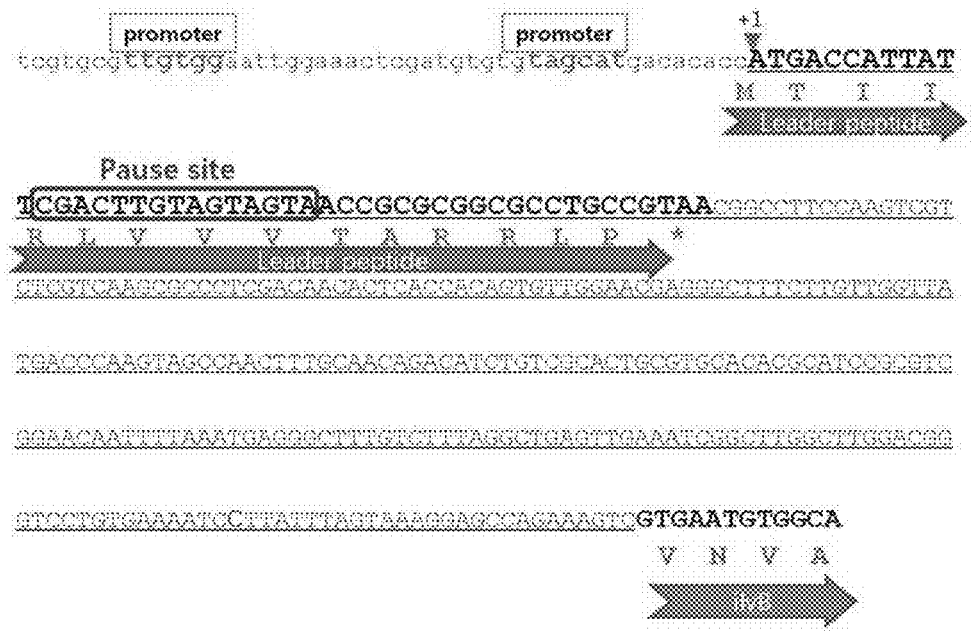
[Fig. 3]
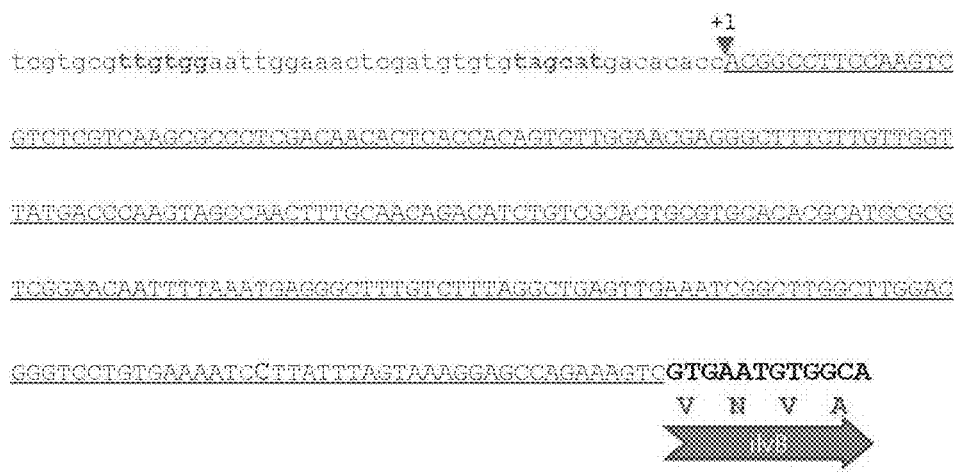

[Fig. 4]
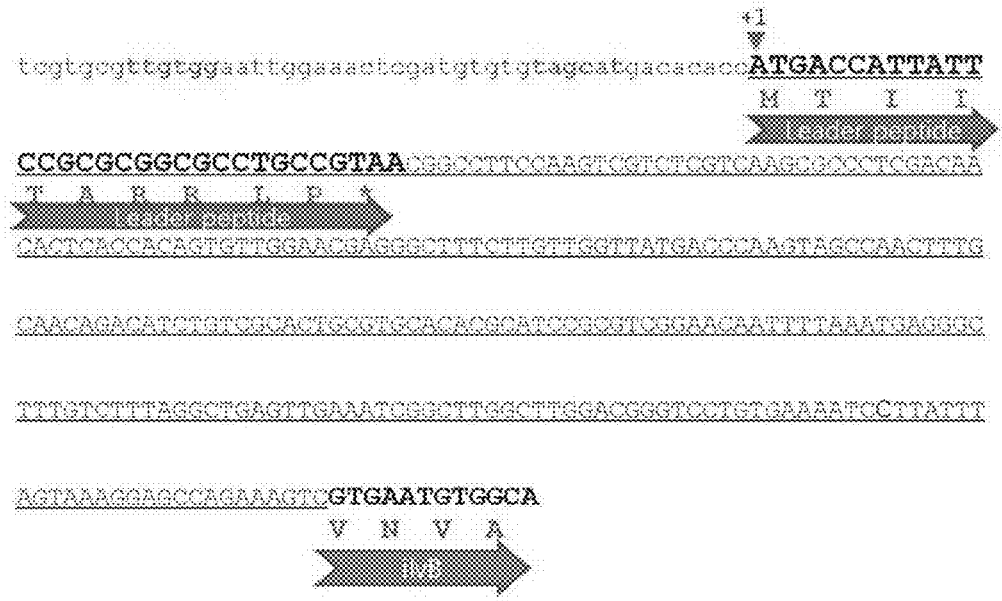
[Fig. 5]
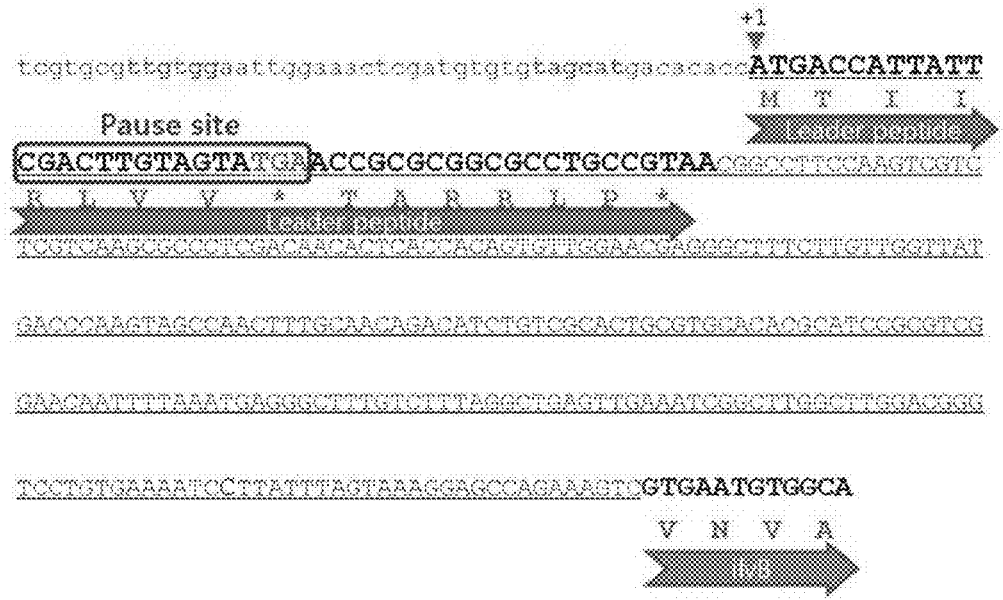

[Fig. 6]

tcgtgcgttgtggaattggaaactcgatgtgtgtagcatgacacaccTGAAATCGGCTTGGC
TTGGACGGGTCCTGTGAAAATCCTTATTTAGTAAAGGAGCCAGAAAGTCGTGAATGTGGCA
                                                  V  N  V  A

SEQUENCE LISTING

```
<160> NUMBER OF SEQ ID NOS: 28

<210> SEQ ID NO 1
<211> LENGTH: 15
<212> TYPE: PRT
<213> ORGANISM: Corynebacterium glutamicum

<400> SEQUENCE: 1

Met Thr Ile Ile Arg Leu Val Val Val Thr Ala Arg Arg Leu Pro
1               5                  10                  15

<210> SEQ ID NO 2
<211> LENGTH: 5
<212> TYPE: PRT
<213> ORGANISM: Corynebacterium glutamicum

<400> SEQUENCE: 2

Arg Leu Val Val Val
1               5

<210> SEQ ID NO 3
<211> LENGTH: 10
<212> TYPE: PRT
<213> ORGANISM: Corynebacterium glutamicum

<400> SEQUENCE: 3

Met Thr Ile Ile Thr Ala Arg Arg Leu Pro
1               5                  10

<210> SEQ ID NO 4
<211> LENGTH: 8
<212> TYPE: PRT
<213> ORGANISM: Corynebacterium glutamicum

<400> SEQUENCE: 4

Met Thr Ile Ile Arg Leu Val Val
1               5

<210> SEQ ID NO 5
<211> LENGTH: 22
<212> TYPE: DNA
<213> ORGANISM: Artificial Sequence
<220> FEATURE:
<223> OTHER INFORMATION: primer for DvalL, DvalP, DvalS

<400> SEQUENCE: 5
gcgcgatgac atctgtgatg tt                                          22

<210> SEQ ID NO 6
<211> LENGTH: 41
<212> TYPE: DNA
<213> ORGANISM: Artificial Sequence
```

```
<220> FEATURE:
<223> OTHER INFORMATION: primer for DvalL

<400> SEQUENCE: 6
agacgacttg gaaggccggt gtgtcatgct acacacatcg a            41

<210> SEQ ID NO 7
<211> LENGTH: 38
<212> TYPE: DNA
<213> ORGANISM: Artificial Sequence
<220> FEATURE:
<223> OTHER INFORMATION: primer for DvalL

<400> SEQUENCE: 7
tgtgtgtagc atgacacacc ggccttccaa gtcgtctc                38

<210> SEQ ID NO 8
<211> LENGTH: 23
<212> TYPE: DNA
<213> ORGANISM: Artificial Sequence
<220> FEATURE:
<223> OTHER INFORMATION: primer for DvalL, DvalP, DvalS

<400> SEQUENCE: 8
cagttcttcg tgtgcatcag cct                                23

<210> SEQ ID NO 9
<211> LENGTH: 47
<212> TYPE: DNA
<213> ORGANISM: Artificial Sequence
<220> FEATURE:
<223> OTHER INFORMATION: primer for DvalP

<400> SEQUENCE: 9
tgtagcatga cacaccatga ccattattac cgcgcggcgc ctgccgt      47

<210> SEQ ID NO 10
<211> LENGTH: 38
<212> TYPE: DNA
<213> ORGANISM: Artificial Sequence
<220> FEATURE:
<223> OTHER INFORMATION: primer for DvalP

<400> SEQUENCE: 10
cggcaggcgc cgcgcggtaa taatggtcat ggtgtgtc                38

<210> SEQ ID NO 11
<211> LENGTH: 50
<212> TYPE: DNA
<213> ORGANISM: Artificial Sequence
<220> FEATURE:
<223> OTHER INFORMATION: primer for DvalS

<400> SEQUENCE: 11
cggcaggcgc cgcgcggtca tactacaagt cgaataatgg tcatggtgtg   50

<210> SEQ ID NO 12
<211> LENGTH: 41
<212> TYPE: DNA
<213> ORGANISM: Artificial Sequence
<220> FEATURE:
<223> OTHER INFORMATION: primer for DvalS

<400> SEQUENCE: 12
ccattattcg acttgtagta tgaaccgcgc ggcgcctgcc g            41
```

<210> SEQ ID NO 13
<211> LENGTH: 41
<212> TYPE: DNA
<213> ORGANISM: Artificial Sequence
<220> FEATURE:
<223> OTHER INFORMATION: primer for DvalA

<400> SEQUENCE: 13
cgtccaagcc aagccgattt cagtgtgtca tgctacacac a         41

<210> SEQ ID NO 14
<211> LENGTH: 43
<212> TYPE: DNA
<213> ORGANISM: Artificial Sequence
<220> FEATURE:
<223> OTHER INFORMATION: primer for DvalA

<400> SEQUENCE: 14
ctcgatgtgt gtagcatgac acactgaaat cggcttggct tgg       43

<210> SEQ ID NO 15
<211> LENGTH: 18
<212> TYPE: DNA
<213> ORGANISM: Artificial Sequence
<220> FEATURE:
<223> OTHER INFORMATION: primer for DvalL

<400> SEQUENCE: 15
catgacacac cggccttc                                    18

<210> SEQ ID NO 16
<211> LENGTH: 20
<212> TYPE: DNA
<213> ORGANISM: Artificial Sequence
<220> FEATURE:
<223> OTHER INFORMATION: primer for DvalP

<400> SEQUENCE: 16
atgaccatta ttaccgcgcg                                  20

<210> SEQ ID NO 17
<211> LENGTH: 20
<212> TYPE: DNA
<213> ORGANISM: Artificial Sequence
<220> FEATURE:
<223> OTHER INFORMATION: primer for DvalS

<400> SEQUENCE: 17
acttgtagta tgaaccgcgc                                  20

<210> SEQ ID NO 18
<211> LENGTH: 23
<212> TYPE: DNA
<213> ORGANISM: Artificial Sequence
<220> FEATURE:
<223> OTHER INFORMATION: primer for DvalA

<400> SEQUENCE: 18
gtagcatgac acactgaaat cgg                              23

<210> SEQ ID NO 19
<211> LENGTH: 30
<212> TYPE: DNA
<213> ORGANISM: Artificial Sequence
<220> FEATURE:
<223> OTHER INFORMATION: primer

<400> SEQUENCE: 19
cgaggatcca accggtatcg acaatccaat                                        30

<210> SEQ ID NO 20
<211> LENGTH: 30
<212> TYPE: DNA
<213> ORGANISM: Artificial Sequence
<220> FEATURE:
<223> OTHER INFORMATION: primer

<400> SEQUENCE: 20
ctgtctagaa atcgtgggag ttaaactcgc                                        30

<210> SEQ ID NO 21
<211> LENGTH: 303
<212> TYPE: DNA
<213> ORGANISM: Corynebacterium glutamicum

<400> SEQUENCE: 21
atgaccatta ttcgacttgt agtagtaacc gcgcggcgcc tgccgtaacg gccttccaag        60
tcgtctcgtc aagcgccctc gacaacactc accacagtgt tggaacgagg gctttcttgt      120
tggttatgac ccaagtagcc aactttgcaa cagacatctg tcgcactgcg tgcacacgca      180
tccgcgtcgg aacaatttta aatgagggct tgtctttag gctgagttga aatcggcttg       240
gcttggacgg gtcctgtgaa aatccttatt tagtaaagga gccagaaagt cgtgaatgtg      300
gca                                                                    303

<210> SEQ ID NO 22
<211> LENGTH: 48
<212> TYPE: DNA
<213> ORGANISM: Corynebacterium glutamicum

<400> SEQUENCE: 22
atgaccatta ttcgacttgt agtagtaacc gcgcggcgcc tgccgtaa                    48

<210> SEQ ID NO 23
<211> LENGTH: 15
<212> TYPE: DNA
<213> ORGANISM: Corynebacterium glutamicum

<400> SEQUENCE: 23
cgacttgtag tagta                                                        15

<210> SEQ ID NO 24
<211> LENGTH: 1582
<212> TYPE: DNA
<213> ORGANISM: Corynebacterium glutamicum

<400> SEQUENCE: 24
ttgttgatgc acactttcgc cgtggagttg gggatgatca cggtctcttg tgcaatcgtg        60
cgaattttgg tcgcgcgcat ggtgatctca atgacggtgc cttcgacaac gatgccgttg      120
ccctcaaaac gcacccagtc acccacgccg aattgctttt ccgtcaggat gaaaaatccg      180
gccaagaagt ccgcaacaat cgactgcgca ccaaggccaa tggcagctga cgcaatggtt      240
gccggaatcg cagcgcccgc gagagagaaa ccaaaagcct gcatcgcgga cggcaagc        300 atgaaaaacg ccacaatttg cgcgatataa acgccaacgc cagcgaacgc gagctggttc      360
ttagtggtgt ccgcatcggc tgcagactcc actcgccgct tgataatacg catggccagt      420

| | |
|---|---:|
| cggccgatac gtggaatcaa aaacgccaag accaggataa ttgctacatc aaaaccggta | 480 |
| tcgacaatcc aattccacaa tgaatagagc aaatattgaa tgggtacgcc taaaatcatg | 540 |
| agccaagatt agcgctgaaa agtagcggga gcctgcctga actttgtgag aatcctgatt | 600 |
| ccttaaccga agtgggggag ttttgggggt gggaattttc gtgcgttgtg aattggaaa | 660 |
| ctcgatgtgt gtagcatgac acaccggcct tccaagtcgt ctcgtcaagc gccctcgaca | 720 |
| acactcacca cagtgttgga acgagggctt tcttgttggt tatgacccaa gtagccaact | 780 |
| ttgcaacaga catctgtcgc actgcgtgca cacgcatccg cgtcggaaca attttaaatg | 840 |
| agggctttgt ctttaggctg agttgaaatc ggcttggctt ggacgggtcc tgtgaaaatc | 900 |
| cttatttagt aaaggagcca gaaagtcgtg aatgtggcag cttctcaaca gcccactccc | 960 |
| gccacggttg caagccgtgg tcgatccgcc gccctgagc ggatgacagg tgcacaggca | 1020 |
| attgttcgat cgctcgagga gcttaacgcc gacatcgtgt tcggtattcc tggtggtgcg | 1080 |
| gtgctaccgg tgtatgaccc gctctattcc tccacaaagg tgcgccacgt cctggtgcgc | 1140 |
| cacgagcagg gcgcaggcca cgcagcaacc ggctacgcgc aggttactgg acgcgttggc | 1200 |
| gtctgcattg caacctctgg cccaggcgca accaacttgg ttaccccaat cgctgatgca | 1260 |
| aacttggact ccgttcccat ggttgccatc accggcaggg tcggaagtgg cctgctgggt | 1320 |
| accgatgctt tccaggaagc cgatatccgc ggcatcacca tgccagtgac caagcacaac | 1380 |
| ttcatggtca ccgaccccaa cgacattcca caggcattgg ctgaggcatt ccacctcgcg | 1440 |
| attactggtc gccctggccc tgttctggtg gatattccta aggatgtcca aaacgctgaa | 1500 |
| ttggatttcg tctggccacc aaagatcgac ctgccaggct accgcccagt ttctactccg | 1560 |
| catgctcgac agattgagca gg | 1582 |

<210> SEQ ID NO 25
<211> LENGTH: 1616
<212> TYPE: DNA
<213> ORGANISM: Corynebacterium glutamicum

<400> SEQUENCE: 25

| | |
|---|---:|
| ttgttgatgc acactttcgc cgtggagttg gggatgatca cggtctcttg tgcaatcgtg | 60 |
| cgaattttgg tcgcgcgcat ggtgatctca atgacggtgc cttcgacaac gatgccgttg | 120 |
| ccctcaaaac gcacccagtc acccacgccg aattgctttt ccgtcaggat gaaaaatccg | 180 |
| gccaagaagt ccgcaacaat cgactgcgca ccaaggccaa tggcagctga cgcaatggtt | 240 |
| gccggaatcg cagcgcccgc gagagagaaa ccaaaagcct gcatcgcgga cacggcaagc | 300 |
| atgaaaaacg ccacaatttg cgcgatataa acgccaacgc cagcgaacgc gagctggttc | 360 |
| ttagtggtgt ccgcatcggc tgcagactcc actcgccgct tgataatacg catggccagt | 420 |
| cggccgatac gtggaatcaa aaacgccaag accaggataa ttgctacatc aaaaccggta | 480 |
| tcgacaatcc aattccacaa tgaatagagc aaatattgaa tgggtacgcc taaaatcatg | 540 |
| agccaagatt agcgctgaaa agtagcggga gcctgcctga actttgtgag aatcctgatt | 600 |
| ccttaaccga agtgggggag ttttgggggt gggaattttc gtgcgttgtg aattggaaa | 660 |
| ctcgatgtgt gtagcatgac acaccatgac cattattacc gcgcggcgcc tgccgtaacg | 720 |
| gccttccaag tcgtctcgtc aagcgccctc gacaacactc accacagtgt tggaacgagg | 780 |
| gcttttcttgt tggttatgac ccaagtagcc aactttgcaa cagacatctg tcgcactgcg | 840 |
| tgcacacgca tccgcgtcgg aacaatttta atgagggct tgtctttag ctgagttga | 900 |
| aatcggcttg gcttggacgg gtcctgtgaa aatccttatt tagtaaagga gccagaaagt | 960 |

-continued

```
cgtgaatgtg gcagcttctc aacagcccac tcccgccacg gttgcaagcc gtggtcgatc      1020
cgccgcccct gagcggatga caggtgcaca ggcaattgtt cgatcgctcg aggagcttaa      1080
cgccgacatc gtgttcggta ttcctggtgg tgcggtgcta ccggtgtatg acccgctcta      1140
ttcctccaca aaggtgcgcc acgtcctggt gcgccacgag cagggcgcag ccacgcagc       1200 aaccggctac gcgcaggtta ctggacgcgt tggcgtctgc attgcaacct ctggcccagg      1260
cgcaaccaac ttggttaccc caatcgctga tgcaaacttg actccgttc ccatggttgc       1320 catcaccggc caggtcggaa gtggcctgct gggtaccgat gctttccagg aagccgatat      1380
ccgcggcatc accatgccag tgaccaagca caacttcatg gtcaccgacc caacgacat      1440 tccacaggca ttggctgagg cattccacct cgcgattact ggtcgccctg ccctgttct       1500 ggtggatatt cctaaggatg tccaaaacgc tgaattggat ttcgtctggc caccaaagat      1560
cgacctgcca ggctaccgcc cagtttctac tccgcatgct cgacagattg agcagg          1616
```

<210> SEQ ID NO 26
<211> LENGTH: 1631
<212> TYPE: DNA
<213> ORGANISM: Corynebacterium glutamicum

<400> SEQUENCE: 26

```
ttgttgatgc acactttcgc cgtggagttg gggatgatca cggtctcttg tgcaatcgtg        60
cgaattttgg tcgcgcgcat ggtgatctca atgacggtgc cttcgacaac gatgccgttg       120
ccctcaaaac gcacccagtc acccacgccg aattgctttt ccgtcaggat gaaaaatccg       180
gccaagaagt ccgcaacaat cgactgcgca ccaaggccaa tggcagctga cgcaatggtt       240
gccggaatcg cagcgcccgc gagagagaaa ccaaaagcct gcatcgcgga cgcaagc         300 atgaaaaacg ccacaatttg cgcgatataa acgccaacgc cagcgaacgc gagctggttc       360
ttagtggtgt ccgcatcggc tgcagactcc actcgccgct tgataatacg catgccagt       420 cggccgatac gtgaatcaa aaacgccaag accaggataa ttgctacatc aaaaccggta        480
tcgacaatcc aattccacaa tgaatagagc aaatattgaa tgggtacgcc taaaatcatg       540
agccaagatt agcgctgaaa agtagcggga gcctgcctga actttgtgag aatcctgatt       600
ccttaaccga agtgggggag ttttgggggt gggaattttc gtgcgttgtg gaattggaaa       660
ctcgatgtgt gtagcatgac acaccatgac cattattcga cttgtagtat gaaccgcgcg       720
gcgcctgccg taacggcctt ccaagtcgtc tcgtcaagcg ccctcgacaa cactcaccac       780
agtgttggaa cgagggcttt cttgttggtt atgacccaag tagccaactt tgcaacagac       840
atctgtcgca ctgcgtgcac acgcatccgc gtcggaacaa ttttaaatga gggctttgtc       900
tttaggctga gttgaaatcg gcttggcttg acgggtcct gtgaaaatcc ttatttagta        960
aaggagccag aaagtcgtga atgtggcagc ttctcaacag cccactcccg ccacggttgc      1020
aagccgtggt cgatccgccg ccctgagcg gatgacaggt gcacaggcaa ttgttcgatc       1080
gctcgaggag cttaacgccg acatcgtgtt cggtattcct ggtggtgcgg tgctaccggt      1140
gtatgacccg ctctattcct ccacaaaggt gcgccacgtc ctggtgcgcc acgagcaggg      1200
cgcaggccac gcagcaaccg gctacgcgca ggttactgga cgcgttggcg tctgcattgc      1260
aacctctggc ccaggcgcaa ccaacttggt taccccaatc gctgatgcaa acttggactc      1320
cgttcccatg gttgccatca ccggccaggt cggaagtggc ctgctgggta ccgatgcttt      1380
ccaggaagcc gatatccgcg gcatcaccat gccagtgacc aagcacaact tcatggtcac      1440
```

| | |
|---|---|
| cgaccccaac gacattccac aggcattggc tgaggcattc cacctcgcga ttactggtcg | 1500 |
| ccctggccct gttctggtgg atattcctaa ggatgtccaa aacgctgaat tggatttcgt | 1560 |
| ctggccacca aagatcgacc tgccaggcta ccgcccagtt tctactccgc atgctcgaca | 1620 |
| gattgagcag g | 1631 |

<210> SEQ ID NO 27
<211> LENGTH: 1403
<212> TYPE: DNA
<213> ORGANISM: Corynebacterium glutamicum

<400> SEQUENCE: 27

| | |
|---|---|
| ttgttgatgc acactttcgc cgtggagttg gggatgatca cggtctcttg tgcaatcgtg | 60 |
| cgaattttgg tcgcgcgcat ggtgatctca atgacggtgc cttcgacaac gatgccgttg | 120 |
| ccctcaaaac gcacccagtc acccacgccg aattgctttt ccgtcaggat gaaaaatccg | 180 |
| gccaagaagt ccgcaacaat cgactgcgca ccaaggccaa tggcagctga cgcaatggtt | 240 |
| gccggaatcg cagcgcccgc gagagagaaa ccaaaagcct gcatcgcgga cggcaagc | 300 |
| atgaaaaacg ccacaatttg cgcgatataa acgccaacgc cagcgaacgc gagctggttc | 360 |
| ttagtggtgt ccgcatcggc tgcagactcc actcgccgct tgataatacg catggccagt | 420 |
| cggccgatac gtggaatcaa aaacgccaag accaggataa ttgctacatc aaaaccggta | 480 |
| tcgacaatcc aattccacaa tgaatagagc aaatattgaa tgggtacgcc taaaatcatg | 540 |
| agccaagatt agcgctgaaa agtagcggga gcctgcctga actttgtgag aatcctgatt | 600 |
| ccttaaccga agtggggggag ttttgggggt gggaatttc gtgcgttgtg gaattggaaa | 660 |
| ctcgatgtgt gtagcatgac acactgaaat cggcttggct tggacgggtc ctgtgaaaat | 720 |
| ccttatttag taaaggagcc agaaagtcgt gaatgtggca gcttctcaac agcccactcc | 780 |
| cgccacggtt gcaagccgtg gtcgatccgc gcccctgag cggatgacag gtgcacaggc | 840 |
| aattgttcga tcgctcgagg agcttaacgc cgacatcgtg ttcggtattc ctggtggtgc | 900 |
| ggtgctaccg gtgtatgacc cgctctattc ctccacaaag gtgcgccacg tcctggtgcg | 960 |
| ccacgagcag ggcgcaggcc acgcagcaac cggctacgcg caggttactg gacgcgttgg | 1020 |
| cgtctgcatt gcaacctctg gcccaggcgc aaccaacttg gttaccccaa tcgctgatgc | 1080 |
| aaacttggac tccgttccca tggttgccat caccggccag gtcggaagtg gcctgctggg | 1140 |
| taccgatgct ttccaggaag ccgatatccg cggcatcacc atgccagtga ccaagcacaa | 1200 |
| cttcatggtc accgacccca cgacattcc acaggcattg gctgaggcat tccacctcgc | 1260 |
| gattactggt cgcccggcc tgttctggt ggatattcct aaggatgtcc aaaacgctga | 1320 |
| attggatttc gtctggccac caaagatcga cctgccaggc taccgcccag tttctactcc | 1380 |
| gcatgctcga cagattgagc agg | 1403 |

<210> SEQ ID NO 28
<211> LENGTH: 6
<212> TYPE: PRT
<213> ORGANISM: Corynebacterium glutamicum

<400> SEQUENCE: 28

Thr Ala Arg Arg Leu Pro
1               5

STRAIN HAVING ENHANCED L-VALINE PRODUCTIVITY AND L-VALINE PRODUCTION METHOD USING THE SAME

CROSS REFERENCE TO RELATED APPLICATIONS

This application is a National Stage Entry of International Application Serial No. PCT/KR2014/001793, filed on Mar. 5, 2014 (WO 2014/142463), and claims the benefit of Korean Application Serial No. 10-2013-0025528, filed on Mar. 11, 2013, which is hereby incorporated by reference in its entirety for all purposes as if fully set forth herein.

TECHNICAL FIELD

The present invention relates to a strain having enhanced L-valine productivity and a method of producing L-valine using the strain.

Incorporated by reference herein in its entirety is the Sequence Listing entitled "Sequence list.txt", created Aug. 10, 2015, size of 14 kilobytes.

BACKGROUND ART

In a microorganism, L-valine, one of branched-chain amino acids, is biosynthesized starting from pyruvate via acetolactic acid, dihydroxy isovaleric acid, and ketoisovaleric acid. These intermediate metabolic products are produced by a reaction catalyzed by acetohydroxy acid synthase, actohydroxy acid isomeroreductase, dihydroxy acid dehydratase, and transaminase B. However, these enzymes also involve in L-isoleucine biosynthesis starting from ketobytyric acid and pyruvate, and also L-leucine is biosynthesized from ketoisovaleric acid, which is an intermediate metabolic product, via 2-isopropylmalic acid, 3-isopropylmalic acid, and ketoisocaproic acid. Thus, since branched-chain amino acids, i.e. L-valine, L-isoleucine, and L-leucine use same enzymes for their biosynthesis processes, it is known that industrially producing one type of a branched-chain amino acid through fermentation has a difficulty. Moreover, there is a problem that industrial mass production is limited by feedback inhibition caused by L-valine, which is a final product, or a derivative thereof.

After a great deal of effort to develop a strain having enhanced L-valine productivity, the present inventors have completed the present invention by finding that a strain transformed to have an inactivated regulatory region of L-valine operon has superior L-valine productivity to a mother strain.

PRIOR ART DOCUMENTS

Patent Literatures (Patent Literature 1) KR 10-1990-0007948 B1
(Patent Literature 2) KR 10-2008-0025355 A1

DISCLOSURE OF THE INVENTION

Technical Problem

One object of the present invention is to provide a novel L-valine producing strain transformed to enhance expression of L-valine operon by entirely deleting or partially deleting or substituting a nucleotide sequence encoding a leader peptide in a regulatory region of ilvBN operon.

Another object of the present invention is to provide a method of producing L-valine by using the novel L-valine producing strain.

Still another object of the present invention is to provide a regulatory region variant of ilvBN operon.

Technical Solution

An embodiment of the present invention provides a novel L-valine producing strain transformed to release attenuation control of L-valine operon by entirely deleting or partially deleting or substituting a nucleotide sequence encoding a leader peptide in a regulatory region of ilvBN operon, wherein the leader peptide is represented by the amino acid sequence of SEQ ID No: 1.

Another embodiment of the present invention also provides a method of producing L-valine by using the novel L-valine producing strain.

Furthermore, another embodiment of the present invention provides a regulatory region variant of L-valine operon having the amino acid sequence represented by SEQ ID No: 3 or 4.

Advantageous Effects

As above, there is an effect in that a novel L-valine producing strain of the present invention has enhanced L-valine productivity due to an increased expression of acetohydroxy acid synthase, which is an enzyme involved in L-valine biosynthesis, by entirely deleting or partially deleting or substituting a nucleotide sequence encoding a leader peptide in a regulatory region of ilvBN operon, wherein the leader peptide is represented by the amino acid sequence of SEQ ID No: 1.

Further, according to a method of producing L-valine using the novel L-valine producing strain of the present invention, there is an effect of producing L-valine at high efficiency and high yield.

BRIEF DESCRIPTION OF THE DRAWINGS

FIG. 1 is a schematic diagram showing ilvBN operon including: a regulatory region of ilvBN operon of wild-type *Cornebacterium glutamicum* ATCC13032; a regulatory region variant (DvalL) in which an entire nucleotide sequence encoding a leader peptide is deleted; a regulatory region variant (DvalP) in which a pause site in the leader peptide is deleted; a regulatory region variant (DvalS) in which the last amino acid of the pause site in the leader peptide is substituted with a stop codon; and a regulatory region variant (DvalA) in which both the leader peptide and an attenuator are deleted.

FIG. 2 is a detailed diagram showing the regulatory region of ilvBN operon of wild-type *Cornebacterium glutamicum* ATCC13032

FIG. 3 is a detailed diagram of the regulatory region variant (DvalL) of FIG. 1 in which an entire nucleotide sequence encoding the leader peptide is deleted.

FIG. 4 is a detailed diagram of the variant-type regulatory region (DvalP) of FIG. 1 in which the pause site in the leader peptide is deleted.

FIG. 5 is a detailed diagram of the variant-type regulatory region (DvalS) of FIG. 1 in which the last amino acid of the pause site in the leader peptide is substituted with a stop codon.

FIG. 6 is a detailed diagram of the variant-type regulatory region (DvalA) of FIG. 1 in which both the leader peptide and the attenuator are deleted.

MODE FOR CARRYING OUT THE INVENTION

One embodiment of the present invention relates to a novel L-valine producing strain transformed to enhance expression of L-valine operon by entirely deleting or partially deleting or substituting a nucleotide sequence encoding a leader peptide in a regulatory region of ilvBN operon, wherein the leader peptide is represented by the amino acid sequence of SEQ ID No: 1.

In the present invention, the term "L-valine operon (ilvBN operon)" includes a gene ilvBN encoding acetohydroxy acid synthase which is an enzyme involved in a first step of L-valine biosynthesis in an L-valine producing microorganism and synthesizing acetolactate from 2 molecules of pyruvate.

More particularly, the ilvBN operon includes a regulatory region and a structural gene encoding acetohydroxy acid synthase, wherein the regulatory region includes a promoter, a nucleotide sequence encoding a leader peptide, a pause site located in the leader peptide, and an attenuator (see, FIGS. 1 and 2).

In the present invention, the expression of the structural gene encoding the acetohydroxy acid synthase is enhanced by entirely deleting or partially deleting or substituting a nucleotide sequence encoding the leader peptide in the regulatory region of the ilvBN operon, to thereby improve L-valine productivity. Specifically, a site of partial deletion or substitution in a nucleotide sequence encoding the leader peptide may be in the pause site, and more specifically, the end of the pause site may be substituted with a stop codon.

In the present invention, to provide a novel L-valine producing strain transformed to enhance expression of L-valine operon by entirely deleting or partially deleting or substituting a nucleotide sequence encoding the leader peptide in the regulatory region of ilvBN operon as described above, firstly, a recombinant vector having the nucleotide sequence encoding the leader peptide is entirely deleted or the partially deleted or substituted in the regulatory region of ilvBN operon may be constructed.

In a specific example of the present invention, to construct the vector, regulatory regions having an entirely deleted or a partially deleted or substituted nucleotide sequence which encodes the leader peptide in the regulatory region of ilvBN operon (DvalL, DvalP, DvalS) are amplified through polymerase chain reaction using a chromosome of Corynebacterium sp. as a template. Then, the amplified regulatory region is inserted into a vector to construct a recombinant vector. Thereafter, a mother strain is respectively transformed with the recombinant vector.

A vector used for construction of the recombinant vector may be a plasmid, a cosmid, a virus, or a bacteriophage in a native state or a recombinant state. As an example, pWE15, M13, λEMBL3, λEMBL4, λFIXII, λDASHII, λZAPII, λgt10, λgt11, Charon4A, and Charon21A, etc. can be used as a phage vector or a cosmid vector; and pDZ vector, pBR-based, pUC-based, pBluescriptII-based, pGEM-based, pTZ-based, pCL-based and pET-based vector, etc. can be used as a plasmid vector. An available vector is not particularly limited, and also a known expression vector can be used.

In a specific example of the present invention, pDZ was used. The vector pDZ, which is a vector for inserting a chromosome of a microorganism of Corynebacterium sp., is prepared by the method disclosed in Korean Patent Publication No. 2008-0025355.

Recombinant vectors pDZDvalL, pDZDvalP, and pDZDvalS are constructed by respectively inserting the amplified regulatory regions (DvalL, DvalP, and DvalS) into the pDZ vectors.

In the present invention, a mother strain to be transformed by the recombinant vector may be any microorganism capable of producing L-valine without being specifically limited. Specifically, a microorganism of Escherichia sp. or a microorganism of Corynebacterium sp. may be used, more specifically, Corynebacterium glutamicum may be used. Further more specifically, Corynebacterium glutamicum ATCC 13032 may be used as a mother strain. In addition an L-valine producing strain resistants to L-valine or a derivative thereof may be used, specifically, Corynebacterium glutamicum KCCM11201P may be used.

The Corynebacterium glutamicum KCCM11201P, which is the strain disclosed in the present inventor's previously registered Patent No. 10-1117022 is a co-resistant variant having resistance to α-Aminobutyric acid (ABA), α-hydroxyvaline (AHV), thiazole alanine (TA), and Norvaline (NV) in concentration of 20 mM, 20 mM, 40 mM and 50 mM, respectively, when spread on a minimal medium into which α-ABA, AHV TA, and NV are added together, after performing random mutagenesis using Corynebacterium glutamicum KFCC 10661 (Korean Patent Application No. 1988-0016543; Publication No. 1990-0007948) as a mother strain, wherein ABA is an isoleucine derivative and AHV, TA and NV are valine derivatives. The co-resistant variant is an outstanding strain having increased L-valine productivity by 4 times than that of the mother strain Corynebacterium glutamicum KFCC 10661.

It has been found that KCCM11336P, KCCM11337P, and KCCM11338P, which are transformed strains of Corynebacterium glutamicum KCCM11201P with the recombinant vector, have superior L-valine productivity to the mother strain Corynebacterium glutamicum KCCM11201P.

The Corynebacterium glutamicum KCCM11336P is a strain produced by transforming Corynebacterium glutamicum KCCM11201P, with the recombinant vector pDZDvalL. pDZvalL was prepared by inserting the regulatory region variant (DvalL) into pDZ vector, wherein the regulatory region variant (DvalL) has a deletion of a whole nucleotide sequence encoding a leader peptide having the amino acid sequence of SEQ ID No: 1. The Corynebacterium glutamicum KCCM11336P was named as KCJ-456 and deposited with the Korean Culture Center of Microorganism on 19 Nov. 2012 under accession number KCCM11336p.

The Cornebacterium glutamicum KCCM11337P is a strain produced by transforming Cornebacterium glutamicum KCCM11201P, with the recombinant vector pDZDvalP. The pDZvalP was prepared by inserting the regulatory region variant (DvalP) into pDZ vector, wherein the regulatory region variant (DvalP) has a deletion of a pause site in the leader peptide having the amino acid sequence of SEQ ID No: 1. The Cornebacterium glutamicum KCCM11337P was named as KCJ-457 and deposited with the Korean Culture Center of Microorganism on 19 Nov. 2012 under accession number KCCM11337P.

The Cornebacterium glutamicum KCCM11338P is a strain produced by transforming Cornebacterium glutamicum KCCM11201P, with the recombinant vector pDZDvalS. pDZvalS was prepared by inserting the regulatory region variant (DvalS) into pDZ vector, wherein the regulatory region variant (DvalS) has a substitution of the last amino acid of the pause site in the leader peptide having the amino acid sequence of SEQ ID No: 1 with a stop codon. The *Cornebacterium glutamicum* KCCM11338P was named as KCJ-458 and deposited with the Korean Culture Center of Microorganism on 19 Nov. 2012 under accession number KCCM11338P.

Furthermore, in the present invention, expression vectors having the modified regulatory region is constructed to enhance the expression ability of valine biosynthesis. Therefore, provided is an L-valine producing strain by transforming *Corynebacterium glutamicum* ATCC13032, which is a known wild-type strain, using the above expression vectors.

In the present invention, to construct the expression vectors having a modified regulatory region of L-valine operon and valine biosynthetic gene cluster. Nucleotide sequences for vector insertion are amplified through a PCR method by using chromosomes of *Cornebacterium glutamicum* KCCM11201P, *Cornebacterium glutamicum* KCCM11336P, *Corynebacterium glutamicum* KCCM11337P, *Cornebacterium glutamicum* KCCM11338P, and *Cornebacterium glutamicum* KCCM11201P_DvalA as templates. Then, each of the amplified nucleotide sequence is inserted into pECCG117 vector to construct pECCG117-DvalW, pECCG117-DvalL, pECCG117-DvalP, pECCG117-DvalS and pECCG117-DvalA Thereafter, *Cornebacterium glutamicum* ATCC13032 was transformed with the above mentioned vectors, pECCG117-DvalW, pECCG117-DvalL, pECCG117-DvalP, pECCG117-DvalS and pECCG117-DvalA, respectively. L-valine producing strains, *Cornebacterium glutamicum* ATCC13032_DvalW, *Corynebacterium glutamicum* ATCC13032_DvalL, *Cornebacterium glutamicum* ATCC13032_DvalP, *Cornebacterium glutamicum* ATCC13032_DvalS and *Cornebacterium glutamicum* ATCC13032_DvalA, are constructed.

Among those strains, it has been found that *Cornebacterium glutamicum* ATCC13032_DvalL, *Corynebacterium glutamicum* ATCC13032_DvalP, *Cornebacterium glutamicum* ATCC13032_DvalS strains have superior L-valine productivity to *Cornebacterium glutamicum* ATCC13032_DvalW which is transformed to have a regulatory region of an L-valine operon of *Cornebacterium glutamicum* KCCM11201P.

As above, there is an effect in that the novel L-valine producing strain of the present invention has outstanding L-valine productivity due to increased expression of acetohydroxy acid synthase, which is an enzyme involved in L-valine biosynthesis, by entirely deleting or partially deleting or substituting a nucleotide sequence encoding a leader peptide in a regulatory region of ilvBN operon, wherein the leader peptide is represented by the amino acid sequence of SEQ ID No: 1.

Further, another embodiment of the present invention relates to a method of producing L-valine by using the novel L-valine producing strain transformed to enhance expression of L-valine operon by entirely deleting or partially deleting or substituting a nucleotide sequence encoding a leader peptide in a regulatory region of L-valine operon, wherein the leader peptide is represented by the amino acid sequence of SEQ ID No: 1.

To produce L-valine in the present invention, the novel L-valine producing strain of the present invention may be cultured by a widely known method of culturing a microorganism of *Corynebacterium* sp. Specifically, examples of the method of culturing include, but not limited to, batch culture, continuous culture, and fed-batch culture. Such various methods, for example, are disclosed in "Biochemical Engineering" (James M. Lee, Prentice-Hall International Editions, pp 138-176, 1991) etc.

A medium used in culture should meet a requirement of a particular strain in an appropriate manner. A culture medium for a microorganism of *Corynebacterium* sp. is known (see, for example, Manual of Methods for General Bacteriology. American Society for Bacteriology. Washington D.C., USA, 1981). As an available glucose source, included are sugar and carbohydrate such as glucose, saccharose, lactose, fructose, maltose, starch, and cellulose; oil and fat such as soybean oil, sun flower oil, castor oil, and coconut oil; fatty acid such as palmitic acid, stearic acid, and linolenic acid; alcohol such as glycerol and ethanol; and an organic acid such as acetic acid. These materials may be used separately or as a mixture, but it's not limited thereto. As an available nitrogen source, peptone, yeast extract, gravy, malt extract, corn soaking liquid, soybean meal, and urea, or an inorganic compound such as ammonium sulfate, ammonium chloride, ammonium phosphate, ammonium carbonate, and ammonium nitrate may be included. The nitrogen source also may be used separately or as a mixture, but it's not limited thereto. As an available phosphorous source, potassium dihydrogen phosphate, or potassium phosphate dibasic, or corresponding sodium-containing salt may be included, but it's not limited thereto. In addition, a culture medium should contain metal salt required for growth such as magnesium sulfate or iron sulfate. Besides, in addition to these materials, an essential growth product such as an amino acid and vitamin may be included.

Further, an appropriate precursor may be used in a culture medium. Above raw materials may be added to culture during a culturing process in a batch type or a continuous type as appropriately.

pH of culture medium may be adjusted by using a basic compound such as sodium hydroxide, potassium hydroxide, and ammonia or an acidic compound such as phosphoric acid, and sulfuric acid in an appropriate manner. Further, a foam formation may be suppressed by using a antifoaming agent such as fatty acid polyglycol ester. Oxygen or oxygen-containing gas (e.g., air) may be injected into culture medium to maintain an aerobic condition. Temperature of culture may be normally between 20° C. to 45° C. Culturing process may be continued until a maximal produced amount of desired L-valine is obtained. Such goal may be normally achieved within 10 to 160 hours. L-valine may either be secreted to a culture medium or be included in cells.

The method of preparing L-valine of the present invention may further include recovering L-valine from cells or culture medium. As a method of recovering L-valine from cells or culture medium, a method known in the art, for example, centrifugation, filtration, anion exchange chromatography, crystallization and HPLC may be used, but not limited thereto.

According to an example of the present invention, culture was centrifuged at a low speed to remove biomass, and then, obtained supernatant was separated through ion-exchange chromatography.

Hereinafter, the present invention will be described in more detail through examples. However, the examples below are intended to exemplary explain the present invention, and the scope of patent right of the invention is not limited to the examples.

Example 1: Construction of Vector Having Entire Deletion or Partial Deletion or Substitution in Nucleotide Sequence Encoding Leader Peptide for Inactivating Regulatory Region of L-Valine Operon FIGS. 1 and 2 show L-valine operon (ilvBN operon) for synthesizing acetohydroxy acid synthase comprising a structural gene encoding acetohydroxy acid synthase and a regulatory region including a promoter (Pro), a nucleotide sequence encoding a leader peptide, a pause site located in the leader peptide, and an attenuator. Of the regulatory region, as shown in FIG. 1, to amplify regulatory regions variant, amplification was performed through polymerase chain reaction (hereinafter, referred to as "PCR method") using chromosomal DNA of *Cornebacterium glutamicum* ATCC13032 strain, which is purchased from American Type Culture collection (ATCC), as a template, wherein the regulatory region variants to be amplified are as follows: a regulatory region in which an entire nucleotide sequence encoding the leader peptide is deleted (hereinafter, referred to as "DvalL"); a regulatory region variant in which the pause site in the leader peptide is deleted (hereinafter, referred to as "DvalP"); a regulatory region variant in which the last amino acid of the pause site in the leader peptide is substituted with a stop codon (hereinafter, referred to as "DvalS"); and a regulatory region variant in which both the leader peptide and the attenuator are deleted (hereinafter, referred to as "DvalA").

Specifically, to prepare DvalL, firstly, a fragment of about 700 base pairs having BamHI restriction enzyme site in a 5' region was amplified through PCR method using chromosomal DNA of *Cornebacterium glutamicum* ATCC13032 strain as a template and primers of SEQ ID Nos: 5 and 6, wherein a PCR condition was to repeat 30 cycles of: denaturation for one minute at 94° C.; annealing for 30 seconds at 58° C.; and polymerization for 30 seconds at 72° C. with Pfu polymerase.

Secondly, a fragment of about 700 base pairs having XbaI restriction enzyme site in a 3' region was amplified through the PCR method described above using primers of SEQ ID Nos: 7 and 8. Obtained DNA fragments were isolated by GeneAll® Expin™ GEL SV kit (Seoul, Korea), and then used as templates for crossover PCR.

Then, crossover PCR was performed using primers of SEQ ID Nos: 5 and 8 and two DNA fragments obtained above as templates. Specifically, a fragment of about 2000 base pairs was amplified through the PCR method described above. The amplified fragments were treated with restriction enzymes BamHI, and XbaI, and then ligated to pDZ treated with the same enzymes to construct pDZvalL.

To prepare DvalP, firstly, a fragment of about 700 base pairs having BamHI restriction enzyme site in a 5' region was amplified using a chromosome of *Cornebacterium glutamicum* ATCC13032 strain as a template and primers of SEQ ID Nos: 5 and 9.

Secondly, a fragment of about 700 base pairs having XbaI restriction enzyme site in a 3' region was amplified through the PCR method described above using primers of SEQ ID Nos: 10 and 8.

Then, a fragment of about 2000 base pairs was amplified through crossover PCR method described above by using two amplified DNA fragments as templates. The amplified fragments were treated with restriction enzymes BamHI, and XbaI, and then ligated to pDZ treated with the same enzymes to construct pDZvalP.

To prepare DvalS, a fragment of about 700 base pairs having BamHI restriction enzyme site in a 5' region was amplified using a chromosome of *Cornebacterium glutamicum* ATCC13032 strain as a template and primers of SEQ ID Nos: 5 and 11.

Secondly, a fragment of about 700 base pairs having XbaI restriction enzyme site in a 3' region was amplified through the PCR method described above using primers of SEQ ID Nos: 12 and 8.

Then, a fragment of about 2000 base pairs was amplified through crossover PCR method described above using two amplified DNA fragments as templates. The amplified fragments were treated with restriction enzymes BamHI, and XbaI, and then ligated to pDZ treated with the same enzymes to construct pDZvalS.

To prepare DvalA, firstly, a fragment of about 700 base pairs having BamHI restriction enzyme site in a 5' region was amplified using a chromosome of *Cornebacterium glutamicum* ATCC13032 strain as a template and primers of SEQ ID Nos: 5 and 13.

Secondly, a fragment of about 700 base pairs having XbaI restriction enzyme site in a 3' region was amplified through the PCR method described above using primers of SEQ ID Nos: 14 and 8.

Then, a fragment of about 2000 base pairs was amplified by using two amplified DNA fragments as templates through crossover PCR method described above. The amplified fragments were treated with restriction enzymes BamHI, and XbaI, and then ligated to pDZ treated with the same enzymes to construct pDZvalA.

In an amino acid level, sequences of the leader peptide and the pause site are set forth in SEQ ID Nos: 1 and 2, respectively, and amino acid sequences of DvalP and DvalS are set forth in SEQ ID No: 3, and SEQ ID Nos: 4 and 28, respectively.

Further, a nucleotide sequence of an entire regulatory region of L-valine operon, ilvBN, a nucleotide sequence of the leader peptide and a nucleotide sequence of the pause site are set forth in SEQ ID Nos: 21, 22, and 23, respectively. Nucleotide sequences of DvalL, DvalP, DvalS and DvalA are set forth in SEQ ID Nos: 24 to 27, respectively.

Example 2: Construction of Strain Having Inactivated Regulatory Region of L-Valine Operon Derived from L-Valine Producing Strain, *Corynebacterium Glutamicum* KCCM11201P To construct a strain having a modified regulatory region of L-valine operon, an L-valine producing strain *Cornebacterium glutamicum* KCCM11201P was used as a mother strain.

*Cornebacterium glutamicum* KCCM11201P were respectively transformed with pDZDvalL, pDZDvalP, pDZDvalS and pDZDvalA vectors which were constructed in example 1 through electroporation.

Through a second cross-over process, obtained were L-valine producing strains respectively having a modified regulatory region of L-valine operon on a chromosome of *Cornebacterium glutamicum* KCCM11201P.

Base substitution in promoter was finally confirmed by analyzing a nucleotide sequence for a target site; and analyzing whether a gene was amplified or not through PCR when using combination of primer of SEQ ID No 8. and: DvalL and the primer of SEQ ID No. 15; DvalP and the primer of SEQ ID No. 16; DvalS and the primer of SEQ ID No. 17; and DvalA and the primer of SEQ ID No. 18.

Strains transformed with the pDZDvalL, pDZDvalP, and pDZDvalS vectors were named as *Cornebacterium glutamicum* KCJ-456, *Cornebacterium glutamicum* KCJ-457, and *Corynebacterium glutamicum* KCJ-458, respectively, and deposited with the Korean Culture Center of Microorganism on 19 Nov. 2012 under accession number KCCM11336P, KCCM11337P, and KCCM11338P, respectively.

In addition, a strain transformed with pDZDvalA vector was designated as *Cornebacterium glutamicum* KCCM11201P_DvalA.

Example 3: Construction of Overexpression Vector for L-Valine Biosynthesis Having Inactivated Regulatory Region of L-Valine Operon An overexpression vector for L-valine biosynthesis was constructed from *Cornebacterium glutamicum* KCCM11201P which is an L-valine producing strain.

Further, expression vectors having a modified regulatory region of L-valine operon were constructed from each of *Cornebacterium glutamicum* KCCM11336P, *Corynebacterium glutamicum* KCCM11337P, *Cornebacterium glutamicum* KCCM11338P and *Cornebacterium glutamicum* KCCM11201P_DvalA prepared in example 2.

For construction of the vector, using primers of SEQ ID Nos: 19 and 20, genes were amplified through PCR method using chromosomal DNA of *Cornebacterium glutamicum* KCCM11201P, *Cornebacterium glutamicum* KCCM11336P, *Corynebacterium glutamicum* KCCM11337P, *Cornebacterium glutamicum* KCCM11338P and *Cornebacterium glutamicum* KCCM11201P_DvalA as templates. Then, the amplified genes were treated with restriction enzymes BamHI and XbaI, and then inserted into pECCG117 vector treated with the same enzymes to construct respective overexpression vector for L-valine biosynthesis which are pECCG117-DvalW, pECCG117-DvalL, pECCG117-DvalP, pECCG117-DvalS and pECCG117-DvalA.

Example 4: Construction of Overexpression Strain for L-Valine Biosynthesis Having Inactivated Regulatory Region of L-Valine Operon Each of expression vectors, which are pECCG117-DvalW, pECCG117-DvalL, pECCG117-DvalP, pECCG117-DvalS and pECCG117-DvalA as prepared in example 3, was introduced into *Cornebacterium glutamicum* ATCC13032 through electroporation to construct *Cornebacterium glutamicum* ATCC13032_DvalW, *Cornebacterium glutamicum* ATCC13032_DvalL, *Corynebacterium glutamicum* ATCC13032_DvalP, *Cornebacterium glutamicum* ATCC13032_DvalS, and *Cornebacterium glutamicum* ATCC13032_DvalA, respectively. When vector is transformed, kanamycin resistance is achieved. Thus, transformation was confirmed by investigating whether growth occurs or not in a medium including kanamycin in a concentration of 25 µg/ml.

Example 5: L-Valine Production in Strain Having Inactivated Regulatory Region of L-Valine Operon To produce L-valine from each of L-valine producing strains *Cornebacterium glutamicum* KCCM11336P, *Corynebacterium glutamicum* KCCM11337P, *Cornebacterium glutamicum* KCCM11338P and *Cornebacterium glutamicum* KCCM11201P_DvalA prepared in example 2 was cultured as follows. *Cornebacterium glutamicum* KCCM11201P, which is a mother strain, was cultured as control.

In addition, *Cornebacterium glutamicum* ATCC13032_DvalW, *Cornebacterium glutamicum* ATCC13032_DvalL, *Cornebacterium glutamicum* ATCC13032_DvalP, *Corynebacterium glutamicum* ATCC13032_DvalS, and *Cornebacterium glutamicum* ATCC13032_DvalA strains were cultured by the same method above for producing L-valine.

One platinum loop of a strain was inoculated to 250 ml Corner-Baffle flask containing 25 ml of a production medium, and production was performed for 72 hours at 30° C. with 200 rpm. The composition of production medium is shown in table 1 below.

After culture has been completed, an amount of produced L-valine was measured by HPLC. L-valine concentration in a culture medium for each strain was shown in tables 2 and 3 below.

TABLE 1

| Production medium |
| --- |
| Glucose 5%, Ammonium sulfate 2%, Potassium phosphate monobasic 0.1%, Magnesium sulfate heptahydrate 0.05%, Corn Steep Liquid (CSL) 2.0%, Biotin 200 ug/L, pH 7.2 |

TABLE 2

Valine productivity of *Corynebacterium glutamicum* KCCM11201P, KCCM11336P, KCCM11337P, KCCM11338P and KCCM11201P_DvalA

| Strain | L-valine concentration (g/L) |
| --- | --- |
| KCCM11201P | 2.8 |
| KCCM11336P | 3.1 |
| KCCM11337P | 3.2 |
| KCCM11338P | 3.5 |
| KCCM11201P_DvalA | 0.5 |

TABLE 3

Valine productivity of *Corynebacterium glutamicum* ATCC13032_DvalW, ATCC13032_DvalL, ATCC13032_DvalP, ATCC13032_DvalS, and ATCC13032_DvalA

| Strain | L-valine concentration (g/L) |
| --- | --- |
| ATCC13032_DvalW | 0.1 |
| ATCC13032_DvalL | 0.9 |
| ATCC13032_DvalP | 1.1 |
| ATCC13032_DvalS | 1.3 |
| ATCC13032_DvalA | 0.1 |

As shown in table 2, it has been found that a strain transformed to inactivate a regulatory region of L-valine operon, except *Cornebacterium glutamicum* KCCM11201P_DvalA, has improved L-valine productivity than that of an L-valine producing strain *Cornebacterium glutamicum* KCCM11201 which is a mother strain. In particular, *Cornebacterium glutamicum* KCCM11338P showed improved L-valine productivity than that of a mother strain by 25%.

Further, as shown in table 3 above, it has been found that, L-valine producing strains, which are *Corynebacterium glutamicum* ATCC13032_DvalL, *Cornebacterium glutamicum* ATCC13032_DvalP and *Cornebacterium glutamicum* ATCC13032_DvalS strains having a modified regulatory region of L-valine operon, have L-valine productivity 9 to 13 times higher than that of *Cornebacterium glutamicum* ATCC13032_DvalW which is transformed to have a regulatory region of L-valine operon of *Cornebacterium glutamicum* KCCM11201P.

[Explanation of Symbol]

Pro: a promoter,

Leader Peptide: a nucleotide sequence encoding a leader peptide

Pause site: a pause site

Attenuator: an attenuator

Gene: a structural gene

[Accession Number]

Name of deposit organization: Korean Culture Center of Microorganism (international)

Accession number: KCCM11336P

Accession date: 20121119

Name of deposit organization: Korean Culture Center of Microorganism (international)

Accession number: KCCM11337P

Accession date: 20121119

Name of deposit organization: Korean Culture Center of Microorganism (international)

Accession number: KCCM11338P

Accession date: 20121119

The invention claimed is:

1. An L-valine producing strain transformed to enhance expression of L-valine operon by entirely deleting or partially deleting or substituting a nucleotide sequence encoding a leader peptide in a regulatory region of ilvBN operon, wherein the leader peptide is represented by the amino acid sequence of SEQ ID NO: 1.

2. The strain according to claim 1, wherein the leader peptide comprises a pause site of the amino acid sequence represented by SEQ ID NO: 2.

3. The strain according to claim 2, wherein all or part of the nucleotide sequence encoding the pause site is deleted or a part of the nucleotide sequence encoding the pause site is substituted.

4. The strain according to claim 3, wherein 13th to 15th nucleic acids of the nucleotide sequence of SEQ ID NO: 23 encoding the pause site are substituted with a stop codon.

5. The strain according to claim 1, wherein the strain is a microorganism of *Corynebacterium* sp.

6. The strain according to claim 5, wherein the strain is *Corynebacterium glutamicum*.

7. A method of producing L-valine, the method comprising:
    culturing the strain according to claim 1 in a culture medium;
    recovering L-valine from the culture medium of the strain.

8. A regulatory region variant of L-valine operon having an amino acid sequence represented by SEQ ID No: 3, SEQ ID No: 4, or SEQ ID No: 28.

* * * * *